United States Patent [19]
Henderson et al.

[11] Patent Number: 5,085,647
[45] Date of Patent: Feb. 4, 1992

[54] RIGID NEEDLE COVER WITH NEEDLE SEALING PLUG AND METHOD OF MANUFACTURE THEREOF

[75] Inventors: William D. Henderson, Daytona Beach; Roger L. Crouse, Ormond Beach, both of Fla.

[73] Assignee: Sherwood Medical Company, St. Louis, Mo.

[21] Appl. No.: 666,164

[22] Filed: Mar. 7, 1991

[51] Int. Cl.⁵ .............................................. A61M 5/32
[52] U.S. Cl. .................................... 604/192; 604/263
[58] Field of Search ............... 604/192, 197, 198, 199, 604/263

[56] References Cited

U.S. PATENT DOCUMENTS

| | | | |
|---|---|---|---|
| 1,687,502 | 10/1928 | Marcy | 604/263 |
| 2,400,722 | 5/1946 | Swan | 206/43 |
| 2,671,450 | 3/1954 | Dann | 128/218 |
| 2,688,963 | 9/1954 | Smith | 128/216 |
| 2,799,272 | 7/1957 | Peach | 128/221 |
| 2,831,483 | 4/1958 | De Lorenzo | 128/218 |
| 2,907,328 | 10/1959 | Cohen | 128/215 |
| 3,270,743 | 9/1966 | Gingras | 128/215 |
| 3,637,072 | 1/1972 | Narusawa et al. | 206/63.2 R |
| 3,865,236 | 2/1975 | Rycroft | 206/364 |
| 3,889,673 | 6/1975 | Dovey et al. | 128/215 |
| 3,989,045 | 11/1976 | Van Eck | 128/272 |
| 4,088,737 | 4/1978 | Bordow | 128/2 F |
| 4,248,246 | 2/1981 | Ikeda | 604/263 |
| 4,474,734 | 10/1984 | Cooper | 604/263 |
| 4,482,348 | 11/1984 | Dent | 604/198 |
| 4,496,352 | 1/1985 | Soika | 604/263 |
| 4,507,118 | 3/1985 | Dent | 604/198 |
| 4,508,534 | 4/1985 | Garver, Sr. et al. | 604/111 |
| 4,636,201 | 1/1987 | Ambrose et al. | 604/192 |
| 4,728,320 | 3/1988 | Chen | 604/192 |
| 4,735,311 | 4/1988 | Lowe et al. | 206/365 |
| 4,772,272 | 9/1988 | McFarland | 604/198 |
| 4,775,367 | 10/1988 | Schmidt | 604/192 |
| 4,810,248 | 3/1989 | Masters et al. | 604/263 |
| 4,872,552 | 10/1989 | Unger | 206/365 |
| 4,897,083 | 1/1990 | Martell | 604/192 |
| 4,917,679 | 4/1990 | Kronner | 604/198 |
| 4,950,242 | 8/1990 | Alvarez | 604/110 |
| 4,986,818 | 1/1991 | Imbert | 604/263 |

*Primary Examiner*—John D. Yasko
*Assistant Examiner*—Sharon Finkel
*Attorney, Agent, or Firm*—Andrew J. Beck; Montgomery W. Smith; Gene B. Kartchner

[57] ABSTRACT

A needle cover is disclosed which includes an elongate rigid tubular housing having a generally cylindrical central bore. A hollow frusto-conical shaped needle guide, which gradually reduces in diameter toward the distal end of the cover is located within the housing and effectively separates the fore into a proximal chamber and a cylindrical distal chamber. The distal chamber receives and retains a resilient plug which functions as a sealing member to seal the distal lumen opening of a needle cannula. The needle guide includes a distal opening which defines the boundary between the proximal and distal chambers. The guide functions to direct the tip of the needle through the proximal chamber and into the central portion of the resilient plug located in the distal chamber. During manufacture, the resilient plug functions to seal the tip of the needle cannula in a fluid tight seal. The needle cover housing, including the needle guide, is formed as an integral unit. The resilient plug is then inserted into the distal chamber and the end thereof is swagged to permanently secure the plug within the distal chamber in abutting relationship with the distal end surface of the needle guide. The needle guides outer surface, cooperates with a portion of the bore wall and with a portion of the plug insert to form an annular cavity which facilitates manufacture of the cover and decreases the total amount of material required therefor.

19 Claims, 2 Drawing Sheets

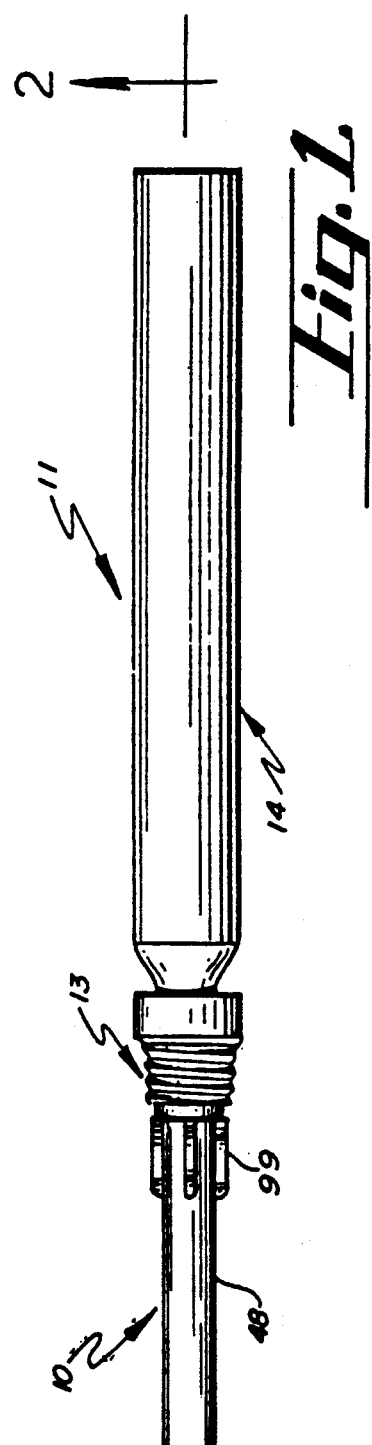
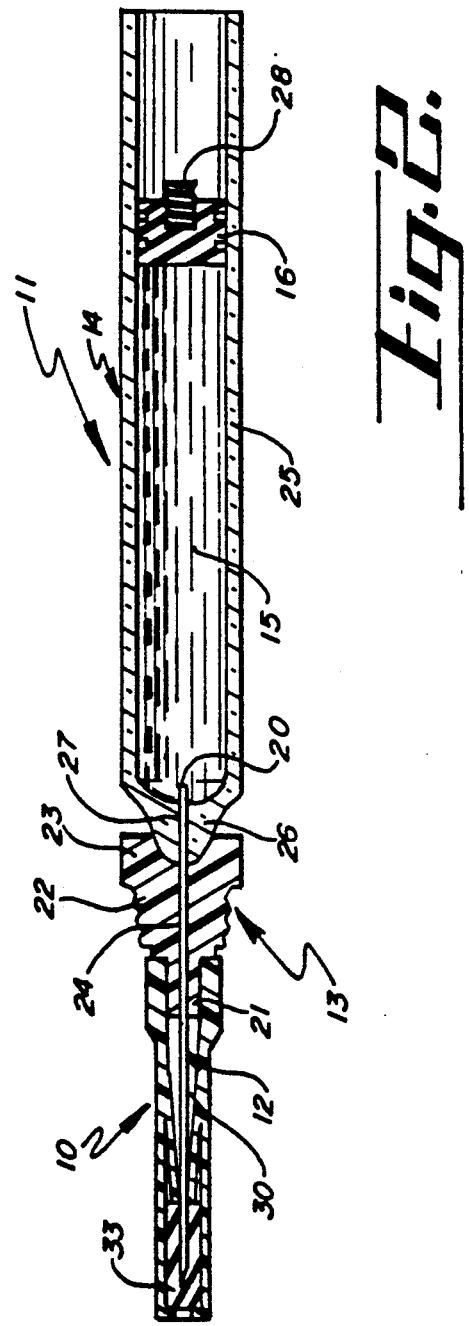

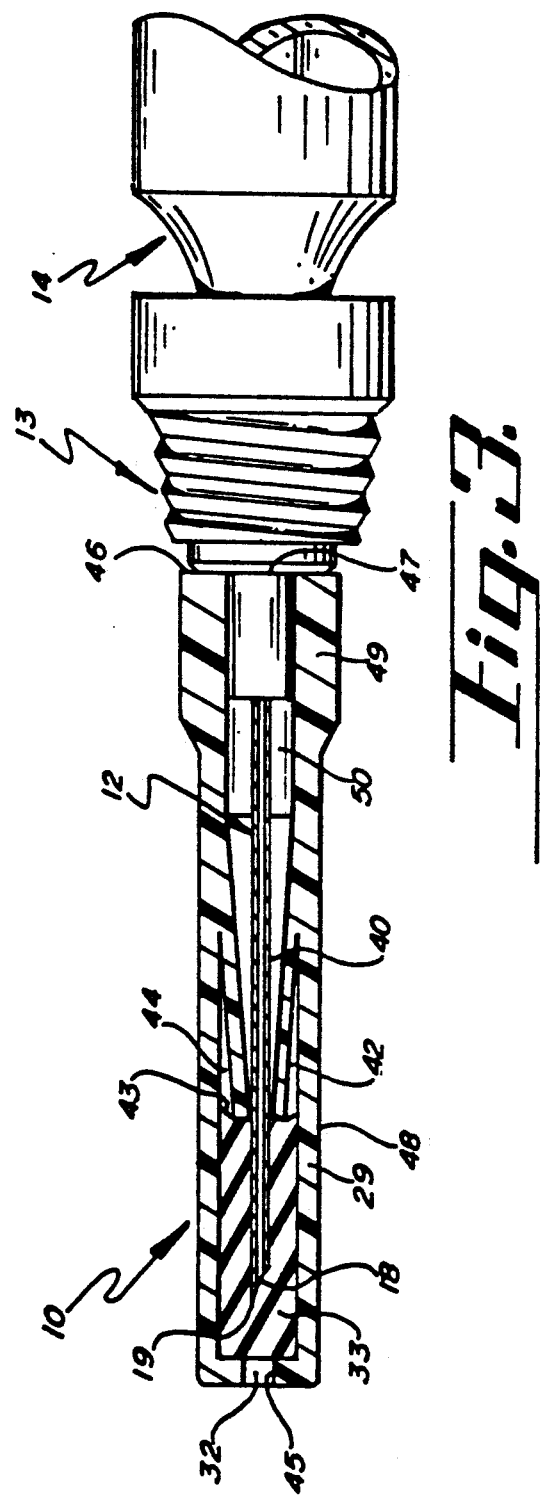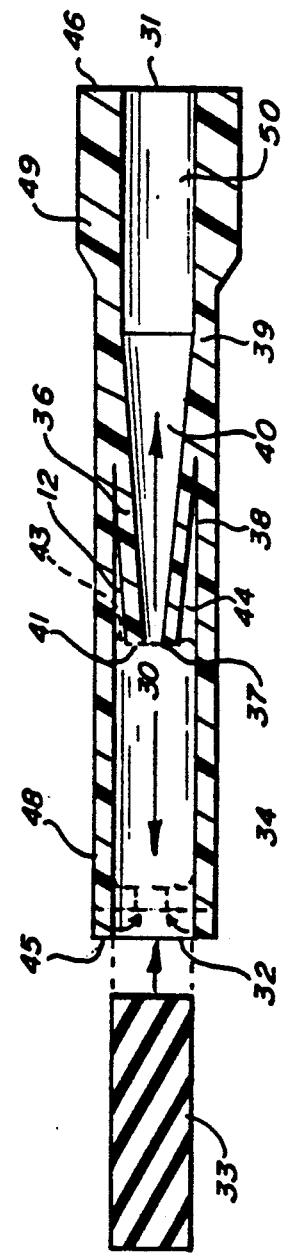

RIGID NEEDLE COVER WITH NEEDLE SEALING PLUG AND METHOD OF MANUFACTURE THEREOF

BACKGROUND OF THE INVENTION

1. Field of the Invention

The present invention relates to a rigid cover for a needle cannula. More specifically, the present invention relates to a rigid cover for protecting and sealing a needle cannula of a prefilled syringe assembly, and methods of manufacturing the cover.

2. Description of the Prior Art

It is common practice in the preparation of medications for use by medical workers, to prepackage the medications directly within a sealed hypodermic syringe assembly when such is a necessary vehicle for administration of the medication to a patient. According to the practice, a hypodermic syringe is prefilled with a predetermined amount of medication, and the medication is sealed into the syringe by sealing the distal end of the needle cannula. The syringe is then packaged singly or in a predetermined quantity, into packaging which can be sterilized to maintain the sterility of the syringes until the medication is to be administered to a patient.

In following this procedure, it has often been the practice to seal the distal end of the needle cannula with a resilient needle sheath. A sheath of this type is usually formed of a resilient rubber material with an elongated cavity therein which can accept the needle cannula. Generally, the sheath is formed so as to be capable of forming a friction fit with the hub of the needle cannula to hold the sheath in position over the needle. The cavity is sized so as to either fit snugly around the distal tip of the needle cannula, or allow the distal tip of the needle cannula to pierce the distal end of the sheath and become embedded therein. In either case, the sheath effectively seals the tip of the needle cannula to prevent fluid from flowing therethrough out of the syringe during storage or prior to use.

Although the resilient needle sheath is generally quite successful in sealing the needle cannula, there remain serious concerns in the use thereof. Specifically, due to the pierceability of the sheath, there exists the possibility of medical workers accidentally receiving a needle stick while using the syringe. This usually occurs either during preparation of the syringe for administration of medication to a patient, or during disposal procedures therefor. For example, since the sheath is formed of a resilient rubber, a minimal force (improperly applied) is all that is needed to cause the needle tip to penetrate, and even pierce completely through, the sheath. Therefore, inadvertent pressure on the tip of the sheath while the needle is properly placed therein, may cause the needle to pierce entirely through the sheath's distal end and become exposed.

Further, medical workers often attempt to reinsert the needle into the sheath after the syringe has been used and prior to its disposal, even though this procedure is generally not recommended. Misalignment of the needle with the sheath during reinsertion can cause the tip of the needle to pierce through the side of the sheath wall and contact the hand of the medical worker holding it. Needle protrusion of this nature can readily occur, since the tip of commonly used needles is ground off center (i.e., on a biases) and therefore does not proceed in a linear path when piercing through the resilient sheath material. Instead, the needle tends to follow the off centered point thereof as it passes through the sheath and in effect "skives off" in an arcing path of travel as it passes through the sheath material. If a medical worker is not extremely careful to let the needle center itself in the sheath cavity during reinsertion, the needle may inadvertently contact the side of the sheath cavity and pierce through the sheath material in a surprisingly unexpected direction, catching the medical worker off guard and likely causing a stick to the hand of the medical worker which is being used to hold the sheath.

Although rigid, substantially impenetrable covers are commonly used to cover needle cannula's of hypodermic syringe assemblies, they are generally unsuitable for use on syringes which have been prefilled with a fluid such as a liquid medicament. This is due to their inability to seal the end of the needle cannula from fluid flow therethrough during storage and prior to use.

There have been attempts in the past to develop a substantially impenetrable cover which can seal the end of a needle cannula commonly used on prefilled syringes, while at the same time provide added protection to a medical worker from accidental needle sticks. An example of a needle cover generally describing the background of the present invention is shown in U.S. Pat. No. 4,735,311 to Lowe et al.

Lowe et al. discloses a needle shield which includes an elongated tubular housing having a central bore which varies in cross-sectional diameter along its entire longitudinal length so as to form a first chamber in the proximal part of the bore which can function to guide the needle into a central position in the shield, and a second chamber in the distal portion of the bore adapted to receive a resilient piercable material. The second chamber is of a diameter slightly larger than the diameter of the resilient piercable insert material, and most importantly, includes a tapered wall at an inner end thereof which forms a diameter less than that of the remaining portion of the chamber. The tapered wall functions to tightly squeeze the insert material into generally hermetic sealing relationship therewith when the insert is force thereagainst.

The Lowe et al. device is assembled by inserting the insert material into the second chamber and then applying a precompression force thereto to cause it to seal against the tapered wall. Heat and pressure are applied to the distal end of the cover to force it to partially collapse over the insert and retain it in its proper position.

Although this invention is a substantial improvement over the use of a resilient sheath alone in preventing accidental needle sticks, it nevertheless contains several drawbacks. Specifically, the Lowe et al. shield requires a substantial amount of material to form the shield itself, due to the incorporation of excessive material inside the bore to form the needle guide surfaces and the proximal and distal chambers.

Further, the tapered portion of the distal chamber is very small, due to the relatively small size of the shield as a whole, and is therefore difficult to accurately manufacture on a mass production basis. Since, the design of the Lowe et al. device relies heavily on the uniformly shaped resilient inserts which must properly seal against the tapered section of the distal chamber in order to create the hermetic seal.

Finally, the method of manufacture of the Lowe et al. device requires a precompression of the insert in order to insure proper seating thereof against the tapered section of the chamber, and requires the compression to be held against the insert until the insert is permanently affixed in place by the deformation of the distal end of the shield. This is an added inconvenience in the manufacturing process.

There exists a need in the art to develop a cover for a needle cannula of a prefilled syringe assembly which can seal the needle against fluid flow therethrough and which also is simple to manufacture and relatively inexpensive.

There further exists a need in the art to develop a needle cover which employs the minimum of material and which does not necessarily include design characteristics which require exacting manufacturing standards in order produce a properly functioning device.

OBJECTS AND SUMMARY OF THE INVENTION

It is an object of the present invention to provide a cover for a needle which substantially aids in avoidance of accidental needle sticks to medical workers using the assembly, and also seals the needle lumen during storage and prior to use.

It is further an object of the present invention to provide a needle cover which employs a minimum of material in the manufacture thereof.

It is another object of the present invention to provide a needle cover which is simple in design to allow for ease of manufacture thereof.

It is further an object of the present invention to provide a streamlined method of manufacture of a needle cover which is adapted for mass manufacturing thereof.

These an other objects are realized in a presently preferred embodiment of a needle cover formed in accordance with the principles of the present invention which comprises a housing of generally cylindrical shape which is formed with a generally cylindrical bore entirely therethrough, the bore defining a generally uniform cross-sectional diameter throughout its entire length and having a proximal and distal opening. The housing also includes a needle guide preferably integrally formed therewith. The guide is preferably formed in a generally hollow frusto-conical shape having an open end which effectively separates the proximal and distal chambers of the bore.

The cover further includes a seal located within the bore between the needle guide and the distal opening. The seal is preferably formed as an insert or plug of resilient material which is placed adjacent and in sealing contact with the distal open end of the frusto-conical needle guide, and held in position by the subsequent deformation of the housing. The deformation at of the distal opening of the housing causes least partial closure thereof to permanently affix the plug in position within the bore.

The hollow frusto-conical needle guide is preferably formed of a conical wall of uniform thickness which extends from the bore wall. The guide, in conjunction with the bore and the plug insert, forms the boundary of a generally annular hollow cavity. The formation of this cavity is useful in limiting the amount of material needed to form the housing, and also allows a simplified sealing of the insert against the guide opening. There is no need to taper the chamber wall, nor to precisely size and compress the plug insert in order to effect a proper seal therebetween. The distal end of the needle guide is preferably formed in a generally flat annular surface which can seal against the proximal surface of the plug, avoiding the necessity of circumferential uniformity of the plug in order to allow uniform sealing therebetween.

The needle cover as formed in accordance with the preferred embodiment of the present invention can be manufactured by forming a housing with a bore therethrough of generally uniform cross-sectional diameter, with a hollow frusto-conical needle guide extending into the bore and being formed integrally with housing. A generally cylindrical resilient plug can then be inserted into the distal end of the bore and subsequently forced into sealing contact with the distal surface of the needle guide by deformation of the distal end opening of the housing. The deformation process can be accomplished without the need for precompression of the plug insert.

These an other objects and advantages of the present invention will become apparent from the following more detailed description, taken in conjunction with the accompanying drawings, in which like elements are identified with like numerals throughout. It should be understood that the preferred embodiment as described herein is presented by way of example and not necessarily by way of limitation.

BRIEF DESCRIPTION OF THE DRAWINGS

FIG. 1 is a side view of a preferred embodiment of a needle cover formed in accordance with the principles of the present invention, affixed to a prefilled hypodermic syringe assembly;

FIG. 2 is a longitudinal cross-sectional view of the needle cover and hypodermic syringe assembly of FIG. 1 taken along line II—II of FIG. 1;

FIG. 3 is an enlarged partial cross-sectional view of the needle cover of FIG. 2, with the distal portion of the hypodermic syringe assembly shown in perspective; and FIG. 4 is an expanded cross-sectional view of a preferred embodiment of a needle cover shown in an intermediate stage of a preferred method of manufacture thereof.

DETAILED DESCRIPTION

In the exemplary drawings, used for purposes of illustration, an embodiment of a needle cover made in accordance with the principles of the present invention is referred to generally by the reference numeral 10. The cover 10 is provided for use with a prefilled hypodermic syringe assembly 11 in order to avoid needle sticks to a medical worker from needle cannula 12.

As best shown in FIGS. 1 and 2, the prefilled hypodermic syringe assembly 11 generally includes a needle cannula 12 affixed by hub 13 to a syringe barrel 14. The barrel 14, commonly made of transparent glass, contains a fluid medicament 15 which is trapped therein by a piston 16.

The needle cannula 12 is formed with a lumen 17 extending through the entire length thereof, which includes a distal opening 18 adjacent the cannulas beveled distal tip 19. A proximal opening 20 of the lumen 17 located at the cannulas proximal end and is in fluid communication with the interior of barrel 14.

The needle cannula 12 is affixed to the barrel 14 by hub 13. The hub 13 is formed of a distal cylindrical portion 21, an intermediate cylindrical portion 22, and a proximal cylindrical portion 23, each of which can function to allow a friction fit of the hub 13 with other elements of the syringe assembly 11 as needed, such as in the manner as will be described below. The hub 13 also includes a cavity 24 through which the needle cannula 12 passes, and an abutment shoulder 47 for abutment of the cover 10 thereagainst when it is properly positioned over the hub 13.

The barrel 14 of the syringe assembly 11 is preferably formed of a generally transparent glass sidewall 25, and includes a closed tip 26 at the distal end thereof. The tip 26 is affixed in fluid tight permanent connection to the cavity 24 of hub 13. The tip 26 also includes a channel 27 through which the needle cannula 12 passes. The needle cannula 12 can be permanently affixed to the channel 27 in any well known fluid tight manner.

During use of the hypodermic assembly 11, the fluid medicament 15 is forced through opening 20 of lumen 17 of the needle cannula 12, by movement of piston 16 in a distal direction along the interior of the barrel 14. Prior to movement of piston 16, a piston arm (not shown) can be attached to threaded extension 28 thereof if desired, for convenience in operating the piston 16. As referred to hereinafter in this disclosure, the structure described as the hypodermic syringe assembly 11 is intended to be understood as describing the needle cannula 12, the hub 13, and the barrel 14.

As best shown in FIGS. 1 and 3, the preferred embodiment of the needle cover 10 of the present invention may include a generally elongate cylindrically-shaped housing 29 formed of a relatively rigid material so as to be generally impermeable to penetration by the needle cannula 12. Any common well known metal or polymeric material exhibiting these characteristics may be used, the preferred embodiment of the present invention being formed of polypropylene.

The housing 29 of the cover 10 has formed therein an elongate generally cylindrical bore 30 which is preferably formed of a generally uniform cross-sectional diameter throughout its entire length, and includes a proximal end opening 31 and a distal end opening 32. The proximal end opening 31 is sized to allow the needle cannula 12 and the distal cylindrical portion 21 of the hub 13 to be inserted therethrough. The distal opening 32 (prior to its deformation which will later be described) is sized to allow insertion of the plug insert 33 therethrough into the bore 30. Later deformation of the opening 32 will hold the plug insert 33 in fixed position in the bore 30.

The bore 30 is separated generally into a proximal chamber 50 and a distal chamber 34 by the needle guide 35. The needle guide 35 is formed into a generally hollow frusto-conical shape, having side wall 36 of generally uniform thickness and an open distal end 37. Distal end 37 effectually separates the proximal chamber 50 from the distal chamber 34. The needle guide 35 is affixed to the inner surface 38 of the bore 30 at a proximal end 39 thereof, in such a manner that a relatively smooth transition occurs from the generally uniform diameter of bore surface 38 to the uniformly reducing diameter of the inner guide surface 40.

The distal opening 37 of the guide 35 is formed by the flat annular distal end surface 41 and is sized to be of a slightly larger diameter than the outer diameter of the needle cannula 12. Of course, the opening 37 can be sized to allow for its use with any size of commonly used needle cannulas, and the particular shown embodiment is not intended to be limited to any particular size or diameter of needle cannula 12.

With the plug insert 33 positioned in distal chamber 34 in the manner shown in FIG. 3, the outer conical surface 42 of the guide 35 cooperates with a portion of the inner surface 38 of the bore 30 and the proximal end surface 43 of the plug insert 33 to form an annular cavity 44. The cavity 44 allows uninterfered abutment between the end surface 43 of the plug insert 33, with the distal end surface 41 of the guide 35. This geometric configuration allows a uniform annular seal to be formed between the surface 41 and the surface 43 (of the guide 35 and the plug 41, respectively) without interference from any other part of the cover 11. Further, the presence of cavity 44 necessarily limits the total amount of material used to form the cover 10, thereby reducing overall per unit manufacturing costs.

As shown in FIG. 4, a preferred method of manufacturing the cover 10 of the present invention includes forming the housing 29 with the needle guide 35 formed integrally therewith in a single manufacturing step, such as injection molding or the like. Subsequently, a plug insert 33 can be inserted into the distal chamber 34 of the bore 30 until the proximal end surface 43 thereof abuts with the distal end surface 41 of the needle guide 35. Once in this position, the distal end 45 forming the distal opening 32 of the housing 29 can be deformed, such as by swagging, to trap the plug insert 33 within the distal chamber 34 insure that the plug insert 33 becomes properly positioned in sealing abutment with the needle guide 35.

If desired, depending on the particular hypodermic syringe assembly 11 being used with the cover 10, certain modifications to the basic design of the needle cover 10 may be incorporated thereinto without departing from the spirit and scope of the present invention. For example, the diameter of the proximal chamber 50 of the bore 30 may be adjusted slightly to conform to the outer diameter of the distal portion 21 of the hub 13 in order to insure a tight frictional fit therebetween. Also, the length of chamber 50 may be adjusted to insure that the proximal end surface 46 of the cover 10 can abut against shoulder 47 of the hub 13 when the cover 10 is properly inserted thereover to allow a positive tactile and/or visual indication that the cover 10 is properly and completely fitted over the needle cannula 12 and the distal hub portion 21.

Further, if desired, reinforcement members 47 may be included on the outer surface 48 of the housing 29 in any well known manner in order to reinforce portions of the housing. For example, as shown in the drawings, the reinforcement members 47 are located at the proximal portion of the cover 10 to reinforce the proximal chamber 50 which must fit over the distal end portion 21 of the hub 13.

Finally, although it is preferred that the housing 29 be of generally uniform thickness, light variations in thickness thereof may be desirable and are contemplated by the present invention. For example, a slight uniform reduction in thickness from the proximal to the distal end of the housing 29 may be desirable from the manufacturing standpoint. Similarly, although the needle guide 35 has been described as having a uniform thickness of wall 36, variations such as uniform reduction of thickness in the distal direction may also be desirable and is also contemplated by the present invention.

It will be apparent from the foregoing, while particular embodiments have been illustrated and described, various other modifications can be made thereto without departing from the spirit and scope of the invention.

Accordingly, it is not intended that the invention be limited, except as by the appended claims.

What is claimed is:

1. A needle cover for a hyperdermic syringe assembly which includes a needle cannula having a lumen and a distal tip, said needle cover comprising:

a relatively rigid housing forming an elongate bore therethrough, said bore having an open distal end and an open proximal end;

a generally hollow frusto-conically-shaped needle guide means having an open proximal end and an open distal end, said open proximal end of said needle guide means being larger in diameter than said open distal end thereof, and said open proximal end of said needle guide means being connected to said housing and located within said bore; and needle sealing means located in said bore between said needle guide means and said open distal end of said bore; said bore, said needle sealing means, and said needle guide means cooperating to form a generally annular hollow cavity which extends circumferentially around said bore between said needle guide means and said needle sealing means; whereby, said housing open distal end functions to hold said needle sealing means within said bore in abutting sealing relationship against said open distal end of said needle guide means, and said annular hollow cavity functions to facilitate sealing between said open distal end of said needle guide means and said needle sealing means;

and whereby, the needle cannula of the syringe assembly can pass through said open proximal end of said bore and be centered within said bore by said needle guide means and pierce said sealing means to seal the tip opening of the needle lumen against fluid flow therethrough.

2. A needle cover according to claim 1 wherein said needle guide means includes an annular distal surface, and said sealing means includes a relatively flat proximal surface against which said annular distal surface abuts.

3. A needle cover according to claim 1 wherein said bore is formed of a generally uniform cross-sectional diameter along substantially its entire length.

4. A needle cover according to claim 1 wherein said housing is generally cylindrical and has a substantially uniform wall thickness throughout a major portion of its length.

5. A needle cover according to claim 1 wherein said needle guide means is formed of a generally uniform thickness throughout its entire length.

6. A needle cover according to claim 1 wherein said sealing means is formed of a resilient material.

7. A needle cover according to claim 6 wherein said resilient material is rubber.

8. A needle cover according to claim 7 wherein said sealing means is a resilient rubber plug insert.

9. A needle cover according to claim 1 wherein said needle guide means is integrally formed with said housing.

10. A needle cover according to claim 1 wherein said open proximal end of said bore includes means for attaching said cover to the syringe assembly.

11. A method of making a needle cover for a hyperdermic syringe assembly which includes a needle cannula, said method comprising the steps of:

forming a relatively rigid housing with an elongate bore therethrough, the elongate bore forming an open proximal end and an open distal end;

forming a generally hollow frusto-conically-shaped needle guide means within the bore between the open proximal and open distal ends thereof, the needle guide means also having an open proximal end and an open distal end, the open proximal end of the needle guide means being larger in diameter than the opened distal end thereof and being connected to the housing within the bore;

inserting a sealing means into the bore between the needle guide means and the open distal end of the bore to form an annular cavity bound by the bore, the sealing means, and the needle guide means, the annular cavity extending circumferentially around the bore between the needle guide means and the needle sealing means; and forming the housing at the distal end opening of the bore to affix the sealing means within the bore in abutting sealing relationship with the distal end opening of the needle guide means.

12. A method according to claim 11 wherein said step of deforming the housing at the distal end opening thereof includes swagging the distal end of the housing against the sealing means.

13. A method according to claim 11 wherein said step of forming a needle guide means includes forming a generally hollow frusto-conically-shaped needle guide means integrally with the housing.

14. A method according to claim 11 wherein said step of forming the needle guide means includes forming the needle guide means of a frusto-conical wall of uniform cross-sectional thickness.

15. A method according to claim 11 wherein said step of forming a relatively rigid housing includes forming the housing of a substantially cylindrical wall of generally uniform thickness throughout its entire length.

16. A method according to claim 11 wherein said step of forming the bore includes forming a bore of a generally uniform diameter throughout a major portion of the length thereof.

17. A method according to claim 11 wherein said step of forming a needle guide means and said step of inserting a sealing means into the bore adjacent the needle guide means cause the formation of the hollow annular cavity bounded by the bore, the needle guide means, and the sealing means.

18. A method according the claim 11 wherein said step of forming a relatively rigid housing includes forming the proximal bore opening thereof to a size to allow the hub of the hypodermic syringe assembly to be insertable therein and retained thereby.

19. A method according to claim 18 wherein said step of forming the bore between the proximal opening and the sealing means also includes forming the bore to a predetermined length such that upon insertion of the needle into the cover, the distal opening of the needle lumen will be sealed in the sealing means simultaneously with the proximal opening of the bore being receiving and retaining the needle hub.

* * * * *